United States Patent
Lethers et al.

(10) Patent No.: US 8,890,887 B2
(45) Date of Patent: Nov. 18, 2014

(54) SYNCHRONIZED IMAGE BROWSING

(75) Inventors: Ann Lethers, Fremont, CA (US); Kenny Li, Fremont, CA (US); Yasunori Ikeno, Santa Clara, CA (US)

(73) Assignee: Olympus Corporation, Shinjuku-ku (JP)

( * ) Notice: Subject to any disclaimer, the term of this patent is extended or adjusted under 35 U.S.C. 154(b) by 255 days.

(21) Appl. No.: 13/460,557

(22) Filed: Apr. 30, 2012

(65) Prior Publication Data
US 2013/0083068 A1    Apr. 4, 2013

Related U.S. Application Data

(60) Provisional application No. 61/541,833, filed on Sep. 30, 2011.

(51) Int. Cl.
*G09G 5/00*    (2006.01)

(52) U.S. Cl.
CPC .......................................... *G09G 5/00* (2013.01)
USPC ........................................................ 345/618

(58) Field of Classification Search
None
See application file for complete search history.

(56) References Cited

U.S. PATENT DOCUMENTS

2008/0118125 A1*  5/2008  Mahesh et al. ................. 382/128
2012/0069049 A1*  3/2012  Howe et al. .................... 345/629

\* cited by examiner

*Primary Examiner* — Phi Hoang
*Assistant Examiner* — Mohammad H Akhavannik
(74) *Attorney, Agent, or Firm* — Squire Patton Boggs (US) LLP (57) ABSTRACT

Image viewing systems, such as clinical medical image viewing systems, can be equipped for image browsing. Such systems may benefit from synchronized image browsing. A method can include displaying a plurality of related images at a same time. The method can also include synchronizing the related images with respect to an operation performed on one of the images. Likewise, an apparatus can include a user interface configured to display a plurality of related images at a same time. The apparatus also includes a synchronizer configured to synchronize the related images with respect to an operation performed on one of the images.

14 Claims, 9 Drawing Sheets

SYNCHRONIZED IMAGE BROWSING

CROSS REFERENCE TO RELATED APPLICATIONS

This application is related to, claims the priority of, and incorporates by reference herein the entirety of U.S. Provisional Patent No. 61/541,833, filed Sep. 30, 2011.

BACKGROUND

1. Field

Image viewing systems, such as clinical medical image viewing systems, can be equipped for image browsing. Such systems may benefit from synchronized image browsing.

2. Description of the Related Art

Within a clinical medical environment, when a specimen is taken from a patient, the specimen can be stained. There are reasons for staining. One reason is that by coloring one part of the specimen, but not another part of the same specimen, a color contrast can be more visible on a microscope slide. On the slide, therefore, visualization of the features of the specimen may become easier, as it may be easier to differentiate parts of the subject.

Another reason for staining can be that a certain part of a specimen cannot be seen easily, even under a microscope. Staining with a certain color may increase viewing ability so that the slide can be reviewed and important features can be identified.

In certain cases, a specimen can be sliced into multiple slices. Each slide can be stained differently for study of different aspects of the specimen.

SUMMARY

A method according to certain embodiments includes displaying a plurality of related images at a same time. The method also includes synchronizing the related images with respect to an operation performed on one of the images.

An apparatus, in certain embodiments, includes a user interface configured to display a plurality of related images at a same time. The apparatus also includes a synchronizer configured to synchronize the related images with respect to an operation performed on one of the images.

According to certain embodiments, an apparatus includes display means for displaying a plurality of related images at a same time. The apparatus also includes synchronization means for synchronizing the related images with respect to an operation performed on one of the images.

BRIEF DESCRIPTION OF THE DRAWINGS

For proper understanding of the invention, reference should be made to the accompanying drawings, wherein.

DETAILED DESCRIPTION

In a digital slide image application, in addition to the techniques described above, a differing image sharpening techniques can be applied to produce various shadings on each scanned image for the same specimen slide. Those images can be used for further study or view. For ease of comparison, the different images or images with different post-processing can be placed side-by-side.

Certain embodiments provide way of arranging slides or digital images to facilitate the simultaneous study of multiple related images. For example, certain embodiments provide ways of synchronizing view of multiple related images.

Figure 1A:
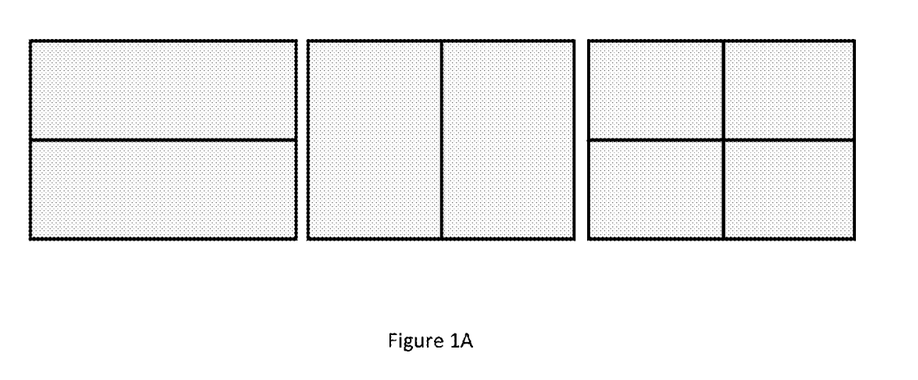
FIG. 1A illustrates the division of a screen into multiple windows.

One aspect of synchronizing view of multiple related images can relates to division of screen space. Synchronized image browsing can be provided in a variety of ways. For example, FIG. 1A illustrates the division of a screen into multiple windows. As shown in FIG. 1A, the screen's real estate can be divided into multiple windows. The division fashion may depend on a business specification. This can allow multiple similar or related images to be displayed at the same time. The diagram in FIG. 1A shows 2 horizontal areas, 2 vertical areas, and 4 quadrant areas as examples. It is also possible for multiple images to be layered on top of one another. For example, each image may be presented within the same boundaries, but images on top may have a degree of transparency or opacity, permitting the user to see the images in effect superimposed on one another.

Next, a synchronization (Sync) function can permit all displayed images to pan, zoom, flip, and rotate at the same time with the same value. The "same value" here may be a value that makes the display of the images appear to undergo the same operation to the same degree. For example, in certain embodiments, the motion may be the same from a display pixel standpoint, but may be scaled or translated with respect to a source pixel standpoint.

The Sync function can be turned on or off. Thus, in an "off" setting the user can set up the individual images at a specific viewing area, angle, rotation, offset, or zoom level first. When all images are adjusted to a desired position, the Sync mode can be turned on to synchronize the subsequent image movements. The Sync function, therefore, can allow the user to focus on an interesting area of the images and not to lose track of related image positions.

Figure 1B:
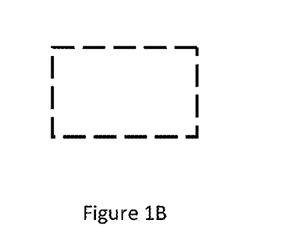
FIG. 1B illustrates a viewing window.
Figure 2:
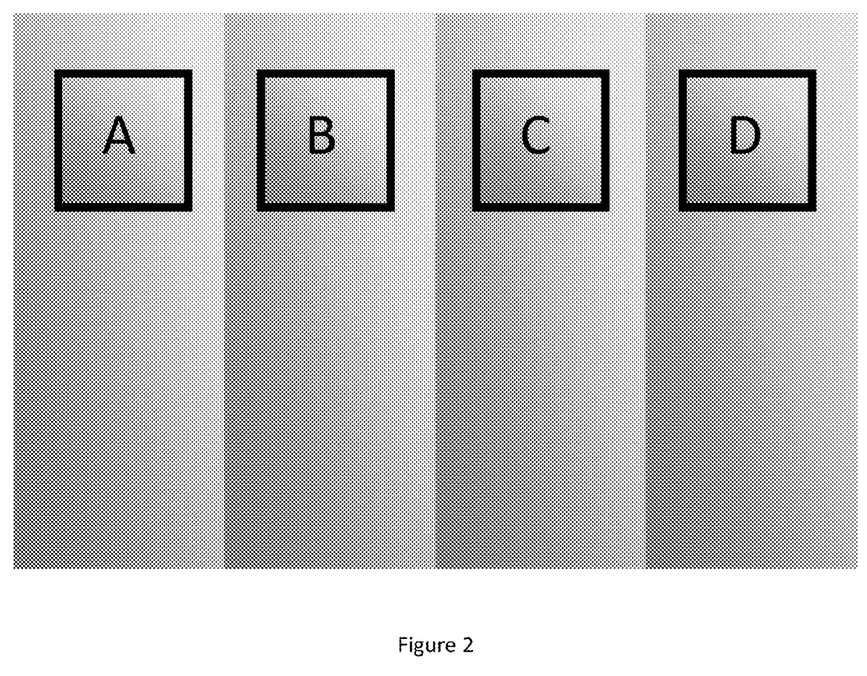
FIG. 2 illustrates a sample image to be viewed.

In Sync mode, a differential value can be kept for panning, zooming, and rotation. FIG. 1B illustrates a viewing window, which can also be referred to as a view window. FIG. 2 illustrates a sample image to be viewed. In FIG. 2, there are four areas, A, B, C, and D shown, which may correspond to four segments of a single image, or may correspond to four slides.

Figure 3:
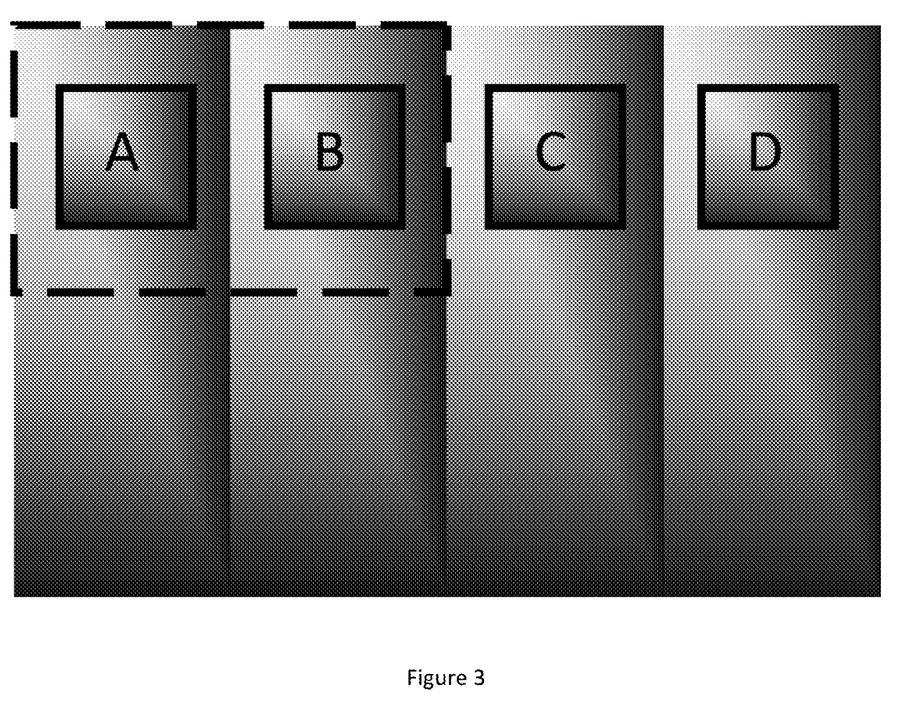
FIG. 3 illustrates a window in the top left of an image.

FIG. 3 illustrates a window in the top left of an image. As can be seen from this example, the underlying image may be larger than the viewing area shown in the window. Thus, in this case, parts of sections A and B are shown in the window, but sections C and D are part of the image, but not shown in the window.

Figure 4:
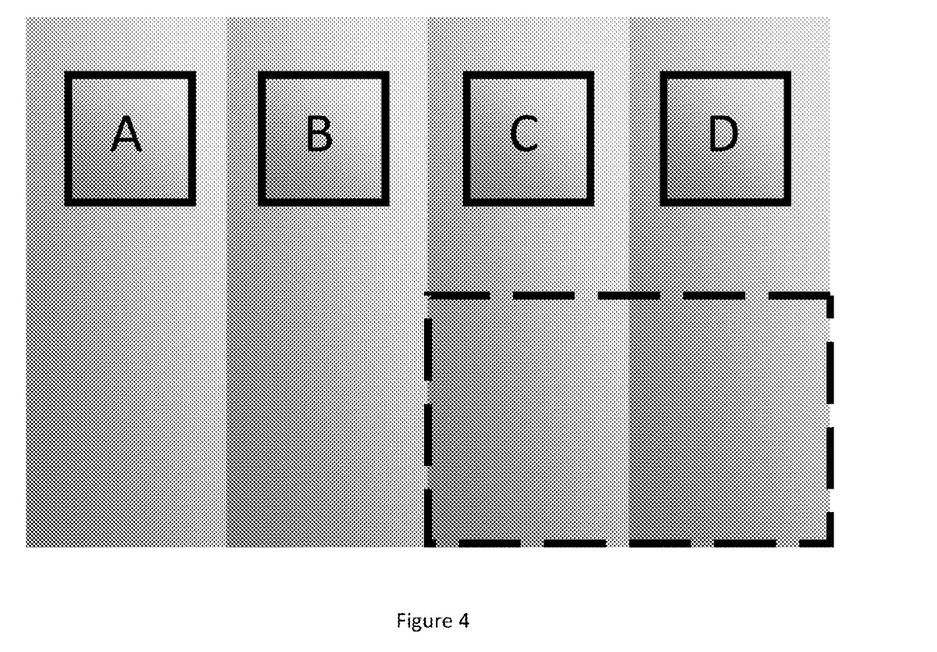
FIG. 4 illustrates another window in the bottom right of another image.

FIG. 4 illustrates another window in the bottom right of another image. As shown in FIG. 4, as with the image in FIG. 3, the image may include various sections A through D. However, in this case, the area of interest, and consequently the area where the second window is viewing, may be in the bottom right corner of the image. This difference in position between the two images may exist for a variety of reasons. For example, two samples may have been placed on respective slides at different positions relative to the slides.

A differential between the top left corner of the window in FIG. 3 and the top left corner of the window in FIG. 4 may be ½ of the image width or one full window width. When the system is in Sync mode, this distance can be maintained during panning the image.

Figure 5:
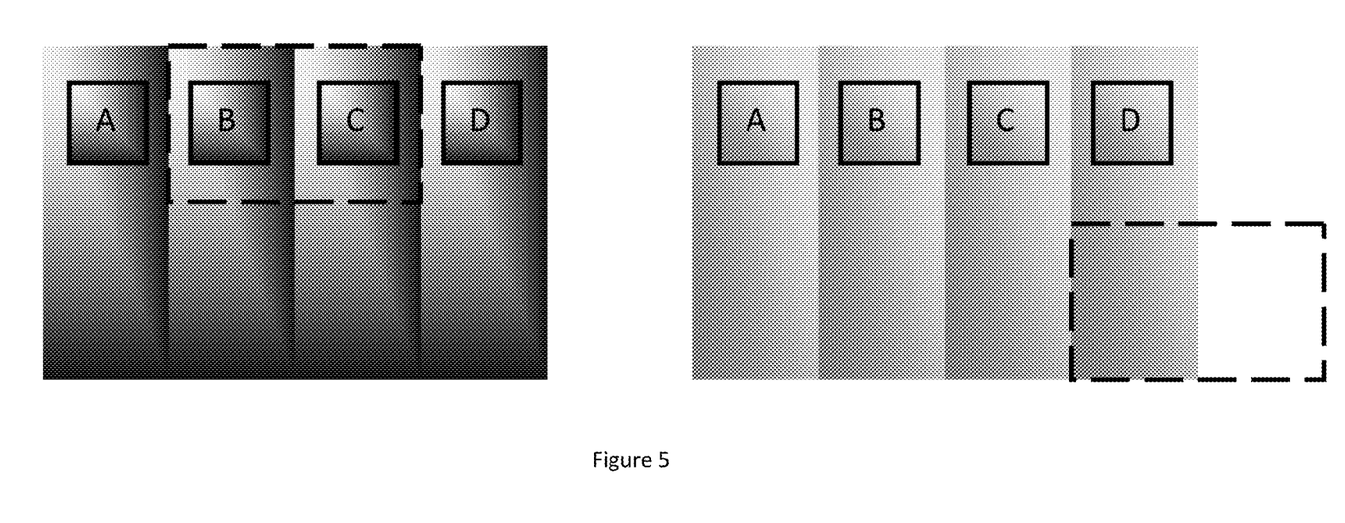
FIG. 5 illustrates two images being panned to the left in synchronization according to certain embodiments.

FIG. 5 illustrates two images being panned to the left in synchronization according to certain embodiments. More particularly, in FIG. 5 both images are panned to the left by ¼ of the image width. Therefore, the second window's image is only includes ¼ of the width of the image, leaving half of the window empty. Nevertheless, the differential between the windows is maintained.

Figure 6:
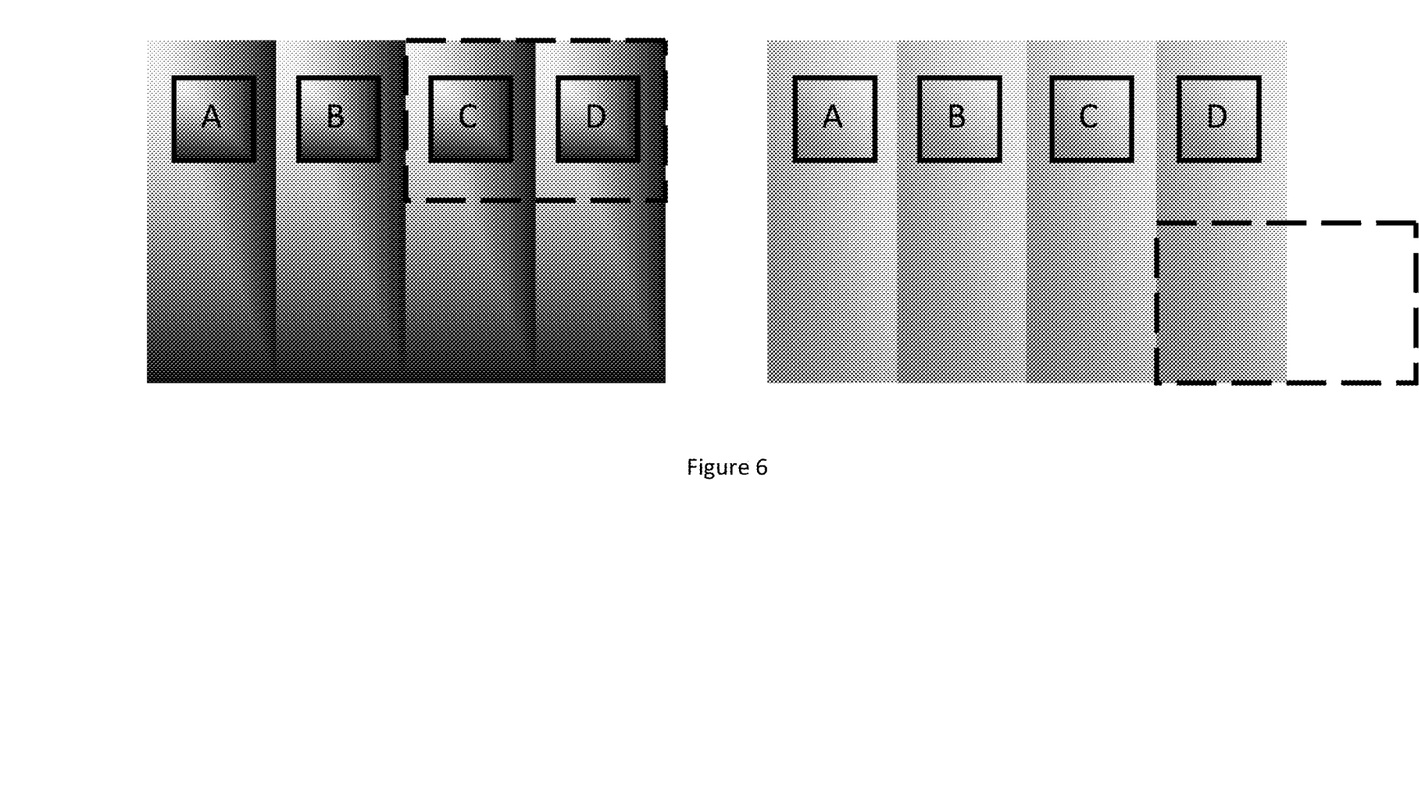
FIG. 6 illustrates an embodiment in which synchronization has been disabled, according to certain embodiments.

FIG. 6 illustrates an embodiment in which synchronization has been disabled, according to certain embodiments. More specifically, in FIG. 6 a first window image is panned to the left by an additional ¼ of the image width beyond that shown in FIG. 5, but the image in the second window has not been panned left any further.

In the case, because the system does not want the image to be out of the field of view (FOV), the second can discontinue or disable panning, even though the first window can continue to pan to the left. The differential is, in this case, broken at this point. However, the system may view this circumstance as an appropriate reason to discontinue the panning. The system can discontinue the panning in the left direction, but may permit scrolling in the up or down direction, in certain embodiments. In certain embodiments, if the user were to continue to pan the image to the left in the first window, the image can reach the limit of the distance it can be panned. Then, the system may not effect any position change, and so no position change will happen to either image, since they are at the edge.

Figure 7:
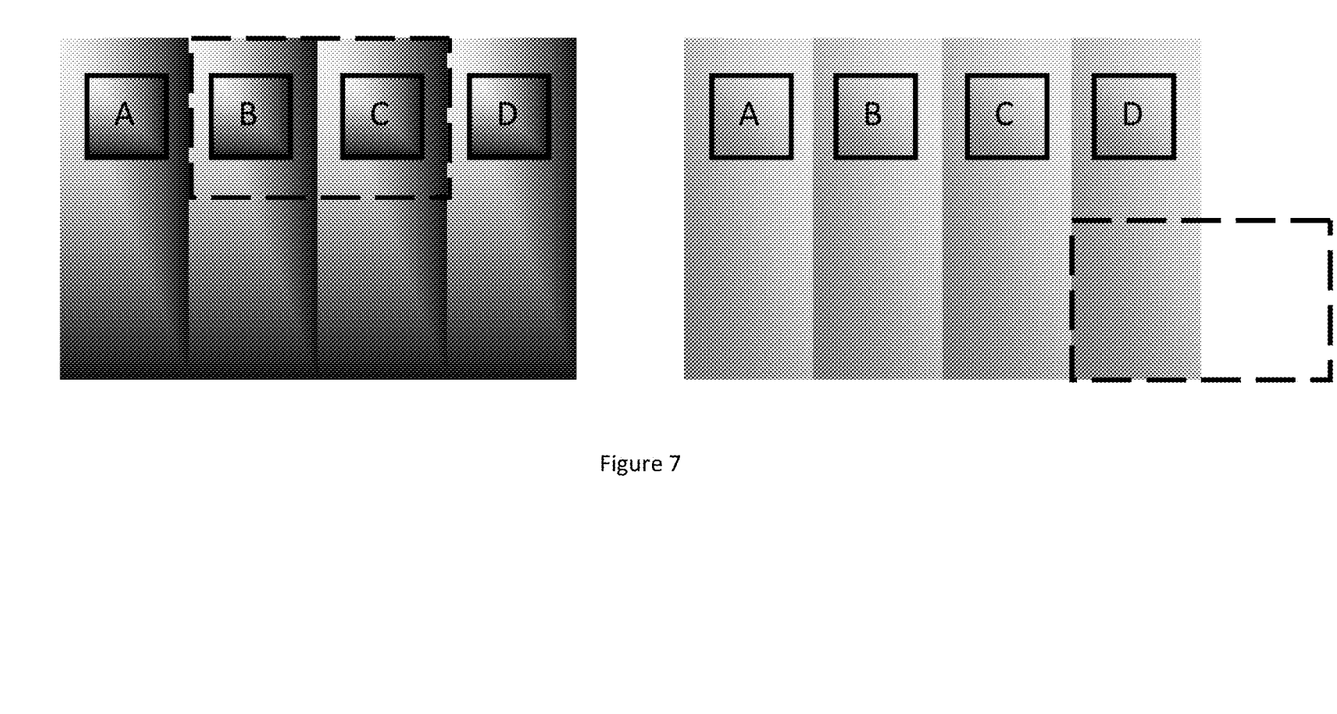
FIG. 7 illustrates an image in a first window panned partly to the right according to certain embodiments.

If the user starts to pan the image to the right while Sync mode is on, based on the series in the preceding figures, it can result in the situation illustrated in FIG. 7, which illustrates an image in a first window panned partly to the right according to certain embodiments. Note that the second window is not changed because the original differential of ½ of the image width is not yet reached.

After the rightward movement of the image of the first window, the original differential is obtained again. Thus, subsequent panning to the right in Sync mode will move both images.

The same process can apply to the image height for panning or scrolling. Rotation and zooming can also have similar rules. There may be no limit of rotation angle, per se, so the differential value may be maintained constantly. In certain cases, however, if the axis of rotation is not in the center of the window, the rotation may have a similar effect to panning in addition to rotating.

Zooming can have a similar limitation as panning. There can be a high and low limit for zoom in and zoom out. If one image reaches it high or low limit, it has to wait until the differential value is reached between two images before it can be zoomed synchronized.

A user can select any number of images to participate in the sync mode. A selected active window can serve as the master. When the master window Sync mode is selected, the differential values for other windows can be initialized by the system. Those values can be maintained as described above for each image until the sync mode is turned off.

It should be noted that other variations of the above can be made. The related images can actually be versions or clones of a same image. For example, a first image can correspond to a first section of a given image and a second image can correspond to a second section of the given image. This may be used, for example, to compare one portion of a microchip scan with another portion of a microchip scan.

The process of image delivery from preparing a slide to presenting the slide image to the user can have imperfections and human errors. A synchronized image browsing feature can compensate or offset the imperfections and errors.

The alignment among multiple slides is not guaranteed to be exactly the same due margins of mechanical accuracy. A synchronized image browsing feature can help the user to look at multiple images at the same time under the same condition.

Moreover, error can occur during the slide preparation. For example, the sample may be placed on the glass slide with the wrong orientation. Thus, for example, if several adjacent slices or cross-sections of tissue are stained in various ways and placed on respective slides, the orientation of the slices may be different on the different slides.

Synchronized image browsing can permit the user to synchronize the image after some corrections, such as flipping, rotation, panning, zooming, or the like, have been performed. Thus, multiple images can be viewed under the same condition as one another.

In another example, a first image of a first tissue sample may have been taken with older scanning equipment and consequently may have a certain maximum resolution, whereas a second image of a second tissue sample may have been taken with newer scanning equipment and consequently may have a higher maximum resolution. A user can adjust the zoom of the second image so that both images are the same size in terms of display pixels (although the source pixels for the same area may be much higher in the second case). Then, the system can synchronize the browsing of the image, while maintaining a fixed relationship with respect to display pixels.

As discussed herein, "zooming" can be a general term, with "zoom out" and "zoom in" being two examples of zooming. Likewise, "panning" and "scrolling" can be general terms that can apply to any direction of panning or scrolling.

Figure 8:
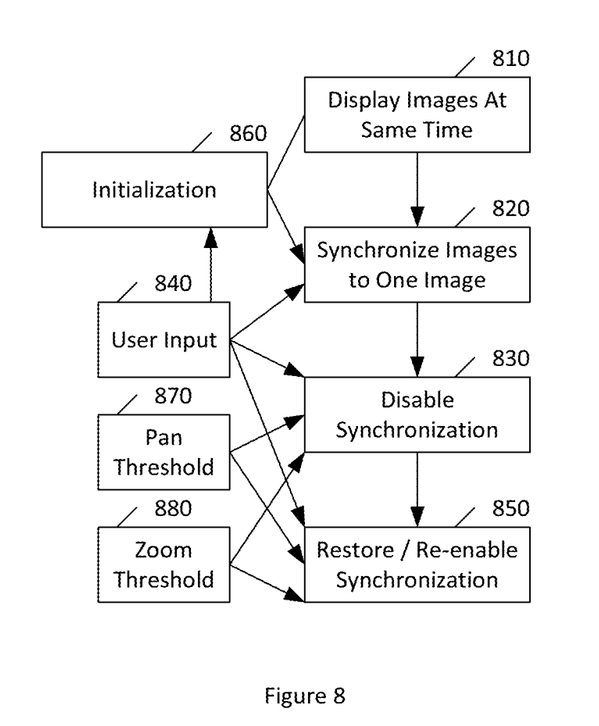
FIG. 8 illustrates a method according to certain embodiments.

FIG. 8 illustrates a method according to certain embodiments. As shown in FIG. 8, a method can include, at 810, displaying a plurality of related images at a same time. The method can also include, at 820, synchronizing the related images with respect to an operation performed on one of the images. The operation can include at least one of pan, zoom, flip, or rotate. The synchronizing can include performing the operation with a same value with respect to display pixels on the related images.

The method can, at 830, further include disabling the synchronizing upon a user request via user input 840. The method can also include, at 850, re-enabling the synchronizing upon a second user request via user input 840.

The method can include permitting or assisting initialization 860 of the related images prior to the synchronizing. The synchronizing can maintain a relationship initialized in the initialization.

The method can also include disabling, at 830, the synchronizing when synchronizing would result in a window being more empty than a threshold amount. This emptiness threshold may be a pan threshold 870. For example, the pan threshold 860 can be set to stop panning due to emptiness when a window would be less than half occupied by the image. The method can further include restoring, at 850, the synchronizing when synchronizing would result in the window being less empty than the threshold amount.

Additionally, the method can include, at 830, disabling the synchronizing when synchronizing would result in a window being zoomed more than a threshold amount, such as an amount indicated in zoom threshold 880. The zoom threshold 880 can be two-fold, including a maximum zoom and a minimum zoom. The zoom threshold 880 can be set based on a minimum quality of picture, either in terms of size or in terms of resolution. The method can additionally include, at 850, restoring the synchronizing when synchronizing would result in the window being zoomed less than the threshold amount.

The method can include initiating the synchronizing at 820 when a master window is selected from a plurality of windows by, for example, a user input 840.

Figure 9:
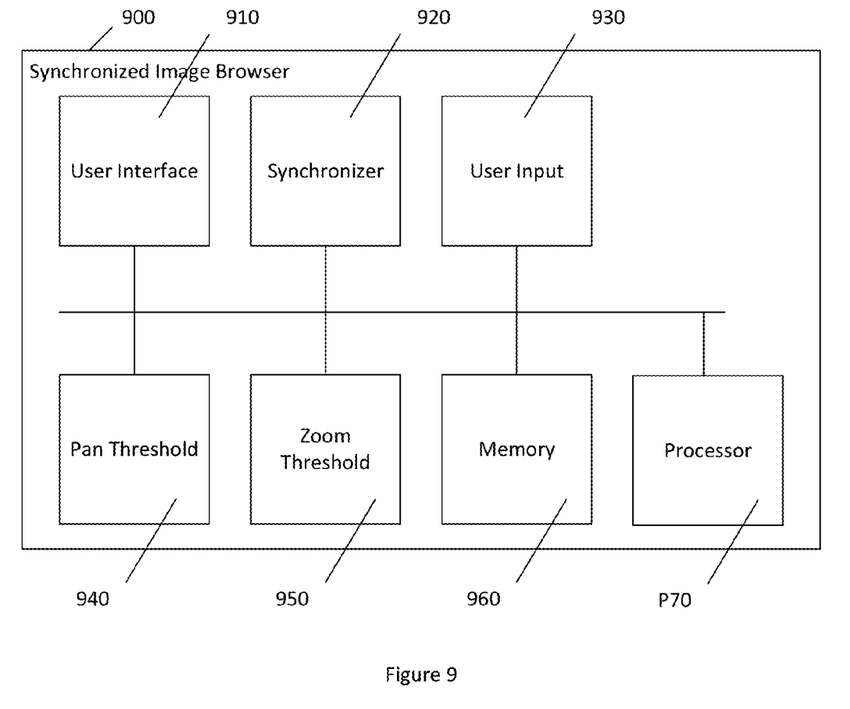
FIG. 9 illustrates a system according to certain embodiments.

FIG. 9 illustrates a system according to certain embodiments. The system may be or include a synchronized image browser. The synchronized image browser 900 may be implemented in hardware only or in software running on hardware. The system may include a user interface 910, which can be configured to display a plurality of related images at the same time. The user interface can permit browsing of the images. The system can also include a synchronizer 920, which can be configured to synchronize the related images with respect to an operation performed on one of the images. The operations can include operations such as panning, flipping, rotating, and zooming.

The synchronizer 920 can maintain a relation, in terms of display pixels, between the related images. For example, if an image in a master window moves 20 display pixels to the left, the image in a slave window can likewise move 20 display pixels to the left, in synchronization with the master window. Alternatively, the relationship maintained can be in terms of source pixels. Thus, if an image in a master window moves 20 source pixels to the left, the image in a slave window can likewise move 20 source pixels to the left, in synchronization with the master window. If the slave window is rotated relative to the source, this approach may result in the synchronization affecting the result. Accordingly, in certain embodiments, in order to maintain similarity of display, if display pixels can be used instead of source pixels as the basis for synchronization.

The system can also include a user input 930. The user input 930 can include an interface to a keyboard, mouse, touchscreen, joystick, trackball, light pen, or any other user input device. The user input 930 can be configured to instruct the synchronizer 920 to disable and re-enable synchronization as well as initializing the drawings and initiating synchronization.

The system can further include pan threshold 940 and zoom threshold 950, which can store or calculate values for maximum panning and/or zooming while in synchronization and can instruct the synchronizer 920 to disable and/or re-enable/restore synchronization when the pan threshold 940 and zoom threshold 950 would be breached in the case of disabling or no longer breached in the case of re-enabling or restoring.

The system can also include at least one memory 960, which can be a memory on a chip, a hard disk drive, or any other kind of information storage device. The memory 960 can be a non-transitory computer-readable medium. The memory 960 can be encoded with instructions that, when executed in hardware, perform a process. The process can include any of the preceding processes, such as the method shown in FIG. 8.

The system can also include at least one processor 970, which can include one or more controllers, application specific integrated circuits (ASICs), central processing units (CPUs), or graphics processing units (GPUs).

One of ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. A method, comprising:
    displaying a plurality of related images at a same time; and
    synchronizing the related images such that a first operation directed by a user to a first image of the related images is performed on the first image and causes a second operation similar in visual effect to the first operation to be automatically performed on a second image of the related images,
    wherein the first operation is a first pan operation on the first image, the second operation is a second pan operation on the second image, the second pan operation is in a movement direction that is the same as that of the first pan operation, and the method further comprises automatically disabling the synchronizing, by stopping the second pan operation on the second image, when the first pan operation on the first image would cause a window, which contains the second image, to be more empty than a pan threshold amount, and
    wherein the disabling is performed by stopping the second pan operation on the second image while continuing the first pan operation directed by the user on the first image.

2. The method of claim 1, wherein the synchronizing is performed such that the first operation directed by the user to the first image causes a window containing the first image to change position according to a number of pixels and a direction, and causes a window containing the second image to automatically move by the same number of pixels and the same direction as the window containing the first image.

3. The method of claim 1, further comprising:
    disabling the synchronizing upon a request by the user, and re-enabling the synchronizing upon a second request by the user.

4. The method of claim 1, wherein the synchronizing is performed such that the first operation directed by the user to the first image results in movement of a window containing the first image and causes the second operation on the second image to move a window containing the second image, wherein there is a differential distance between the window containing the first image and the window containing the second image, and the differential distance before the movements of the windows is the same as after the movements of the windows.

5. The method of claim 1, further comprising after the disabling of the synchronizing, automatically restoring the synchronizing when the first pan operation directed by the user to the first image would cause the window, which contains the second image, to be less empty than the pan threshold amount, wherein the restoring is performed by resuming the second pan operation on the second image such that the first pan operation on the first image and the resumed second pan operation on the second image occur together.

6. An apparatus, comprising:
    a user interface configured to display a plurality of related images at a same time; and a synchronizer configured to synchronize the related images such that a first operation directed by a user to a first image of the related images is performed on the first image and causes a second operation similar in visual effect to the first operation to be automatically performed on a second image of the related images, wherein the first operation is a first pan operation on the first image, the second operation is a second pan operation on the second image, the second pan operation is in a movement direction that is the same as that of the first pan operation, and the synchronizer is further configured to automatically disable synchronization, by stopping the second pan operation on the second image, when the first pan operation on the first image would cause a window, which contains the second image, to be more empty than a pant threshold amount, and the synchronizer is configured to automatically disable the synchronization by stopping the second pan operation on the second image while continuing the first pan operation directed by the user on the first image.

7. The apparatus of claim 6, wherein the synchronizer is configured such that the first operation directed by the user to the first image causes a window containing a first image to change position according to a number of pixels and a direction, and causes the window containing the second image to automatically move by the same number of pixels and the same direction as the window containing the first image.

8. The apparatus of claim 6, wherein the synchronizer is configured to disable synchronization upon a request by the user, and is configured to re-enable synchronization upon a second request by the user.

9. The apparatus of claim 6, wherein the synchronizer is configured such that the first operation directed by the user to the first image results in movement of a window containing the first image and causes the second operation on the second image to move the window containing the second image, wherein there is a differential distance between a window containing the first image and the window containing the second image, and the differential distance before the movements of the windows is the same as after the movements of the windows.

10. The apparatus of claim 6, wherein the synchronizer is further configured, after synchronization was disabled, to automatically restore synchronization, by resuming the second pan operation on the second image, when the first pan operation directed by the user to the first image would result in the window, which contains the second image, being less empty than the pan threshold amount, such that the first pan operation on the first image and the resumed second pan operation on the second image occur together.

11. A method, comprising:
displaying a plurality of related images at a same time; and
synchronizing the related images such that a first operation directed by a user to a first image of the related images is performed on the first image and causes a second operation similar in visual effect to the first operation to be automatically performed on a second image of the related image,
wherein the first operation is a first zoom operation on the first image, the second operation is a second zoom operation on the second image, the second zoom operation is in a zoom direction that is the same as that of the first zoom operation, and the method further comprises automatically disabling the synchronizing, by stopping the second zoom operation on the second image, when the first zoom operation on the first image would cause a window, which contains the second image, to be zoomed more than a zoom threshold amount, and wherein the disabling is performed by stopping the second zoom operation on the second image while continuing the first zoom operation directed by the user on the first image.

12. The method of claim 11, further comprising after the disabling of the synchronizing, automatically restoring the synchronizing when the first zoom operation on the first image would cause the window, which contains the second image, to be zoomed less than the zoom threshold amount, wherein the restoring is performed by resuming the second zoom operation on the second image such that the first zoom operation on the first image and the resumed second zoom operation on the second image occur together.

13. An apparatus, comprising:

a user interface configured to display a plurality of related images at a same time; and a synchronizer configured to synchronize the related images such that a first operation directed by a user to a first image of the related images is performed on the first image and causes a second operation similar in visual effect to the first operation to be automatically performed on a second image of the related images, wherein the first operation is a first zoom operation on the first image, the second operation is a second zoom operation on the second image, the second zoom operation is in a zoom direction that is the same as that of the first zoom operation, and the synchronizer is further configured to automatically disable synchronization, by stopping the second zoom operation on the second image, when the first zoom operation on the first image would cause a window, which contains the second image, to be zoomed more than a zoom threshold amount, and wherein the synchronizer is configured to automatically disable the synchronization by stopping the second zoom operation on the second image while continuing the first zoom operation directed by the user on the first image.

14. The apparatus of claim 13, wherein the synchronizer is further configured, after synchronization was disabled, to automatically restore synchronization, by resuming the second zoom operation on the second image, when the first zoom operation on the first image would cause the window, which contains the second image, to be zoomed less than the zoom threshold amount, such that the first zoom operation on the first image and the resumed second zoom operation on the second image occur together.

* * * * *